United States Patent
Sugito et al.

(10) Patent No.: US 11,791,304 B2
(45) Date of Patent: Oct. 17, 2023

(54) METHOD FOR BONDING INSULATED COATING WIRE, CONNECTION STRUCTURE, METHOD FOR STRIPPING INSULATED COATING WIRE AND BONDING APPARATUS

(71) Applicant: KAIJO CORPORATION, Tokyo (JP)

(72) Inventors: Akio Sugito, Tokyo (JP); Susumu Majima, Tokyo (JP); Mami Kushima, Tokyo (JP)

(73) Assignee: KAIJO CORPORATION, Tokyo (JP)

( * ) Notice: Subject to any disclaimer, the term of this patent is extended or adjusted under 35 U.S.C. 154(b) by 297 days.

(21) Appl. No.: 17/278,537

(22) PCT Filed: Nov. 7, 2019

(86) PCT No.: PCT/JP2019/043584
§ 371 (c)(1),
(2) Date: Mar. 22, 2021

(87) PCT Pub. No.: WO2020/208850
PCT Pub. Date: Oct. 15, 2020

(65) Prior Publication Data
US 2021/0358881 A1    Nov. 18, 2021

(30) Foreign Application Priority Data

Apr. 9, 2019   (WO) ................. PCT/JP2019/015412

(51) Int. Cl.
*H01L 23/00*    (2006.01)
(52) U.S. Cl.
CPC ............. *H01L 24/78* (2013.01); *H01L 24/45* (2013.01); *H01L 24/48* (2013.01); *H01L 24/49* (2013.01);
(Continued)

(58) Field of Classification Search
CPC ....................................................... H01L 24/85
See application file for complete search history.

(56) References Cited

U.S. PATENT DOCUMENTS

| 6,027,009 A | * | 2/2000 | Shinchi | ................. | H01R 4/024 |
| | | | | | 228/111.5 |
| 2008/0197168 A1 | * | 8/2008 | Horino | ................. | B08B 7/0035 |
| | | | | | 228/8 |

FOREIGN PATENT DOCUMENTS

| JP | 58-122742 | 7/1983 |
| JP | 63-248578 | 10/1988 |

(Continued)

OTHER PUBLICATIONS

International Search Report dated Dec. 24, 2019 in International (PCT) Application No. PCT/JP2019/043584.

*Primary Examiner* — Yu-Hsi D Sun
(74) *Attorney, Agent, or Firm* — Wenderoth, Lind & Ponack, L.L.P.

(57) ABSTRACT

Provided is a method for bonding an insulated coating wire, which is capable of stably bonding a metal wire in an insulated coating wire and an electrode. One aspect of the present invention provides a method for bonding an insulated coating wire for electrically connecting a first electrode 12 and a second electrode to each other by an insulated coating wire 11 in which a metal wire is coated with an organic substance, the method including: a step (a) for placing the insulated coating wire 11 onto the first electrode 12; a step (b) for exposing a metal wire from the insulated coating wire; and a step (c) for forming a first bump over the exposed metal wire and the first electrode to electrically connect the metal wire to the first electrode.

11 Claims, 10 Drawing Sheets

(52) U.S. Cl.
CPC ...... *H01L 24/85* (2013.01); *H01L 2224/4569* (2013.01); *H01L 2224/45565* (2013.01); *H01L 2224/48137* (2013.01); *H01L 2224/48227* (2013.01); *H01L 2224/48465* (2013.01); *H01L 2224/48472* (2013.01); *H01L 2224/49175* (2013.01); *H01L 2224/7855* (2013.01); *H01L 2224/78301* (2013.01); *H01L 2224/78316* (2013.01); *H01L 2224/78353* (2013.01); *H01L 2224/78901* (2013.01); *H01L 2224/85045* (2013.01); *H01L 2224/85205* (2013.01); *H01L 2224/85238* (2013.01)

(56) References Cited

FOREIGN PATENT DOCUMENTS

| | | |
|---|---|---|
| JP | 5-74833 | 3/1993 |
| JP | 5-74874 | 3/1993 |
| JP | 5-129357 | 5/1993 |
| JP | 6-291160 | 10/1994 |
| JP | 2000-323515 | 11/2000 |
| JP | 2011-28923 | 2/2011 |
| WO | 2014/077232 | 5/2014 |
| WO | 2014/171160 | 10/2014 |

\* cited by examiner

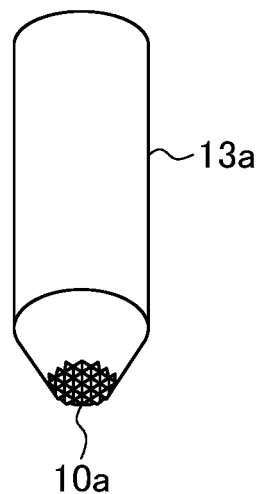 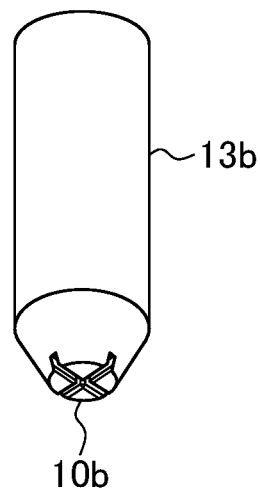 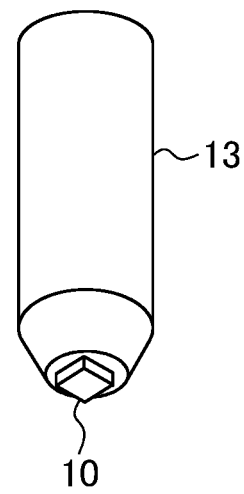
FIG. 5A  FIG. 5B  FIG. 5C
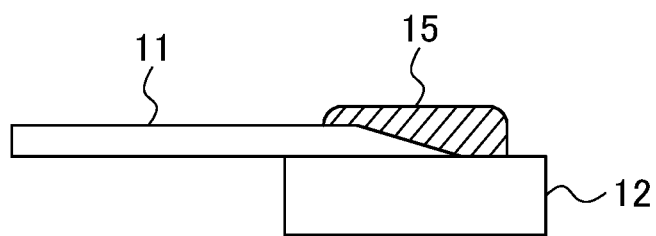
FIG. 6

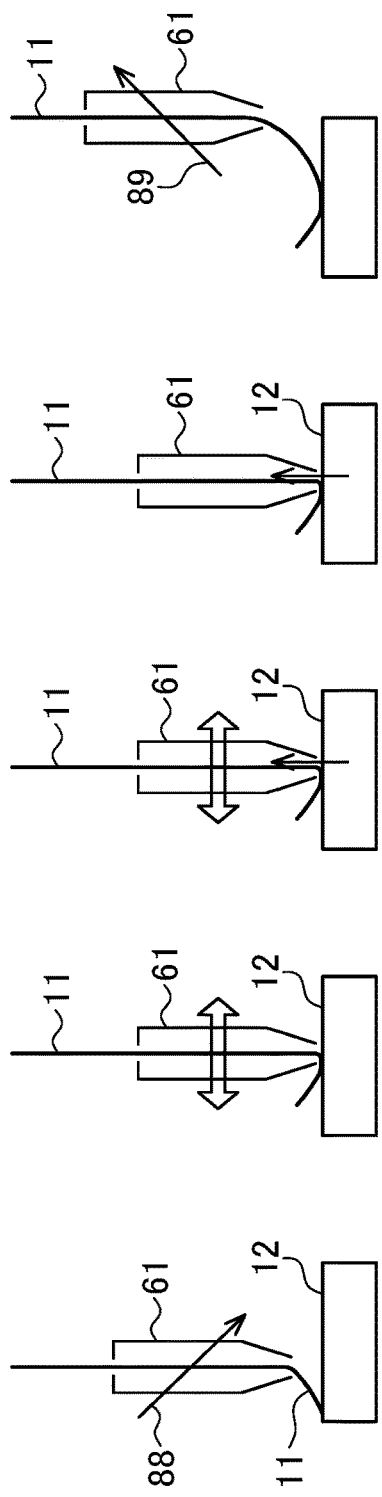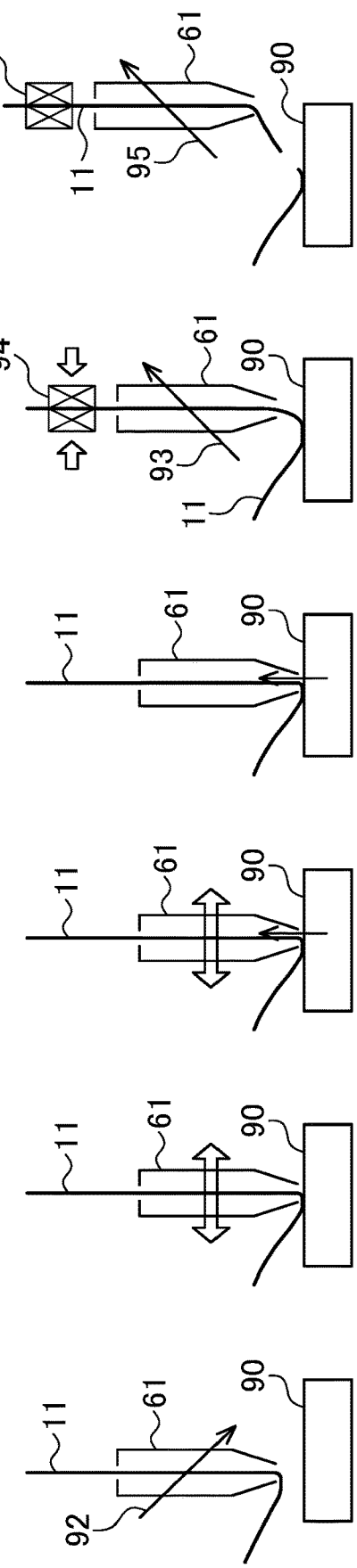

METHOD FOR BONDING INSULATED COATING WIRE, CONNECTION STRUCTURE, METHOD FOR STRIPPING INSULATED COATING WIRE AND BONDING APPARATUS

TECHNICAL FIELD

The present invention relates to a method for bonding an insulated coating wire, a connection structure, a method for stripping an insulated coating wire, and a bonding apparatus.

BACKGROUND ART

In general, wire bonding is performed with metal bare wires. For prevention of short circuit in high density wiring and for wiring in devices that directly contact with human bodies in medical fields, however, insulated coating wires as metal wires that are insulated and coated with organic substances are used.

Examples of electronic parts used in fields of medical apparatus include a self-contained sensor and a self-contained brain-machine interface (BMI) apparatus. In the case of products that directly contact with human bodies as represented by such a sensor, if a wire rod is bonded to an electrode in the sensor, an insulated coating wire in which a wire rod is coated with an insulated coating needs to be used in order to prevent a metal wire rod from affecting human bodies. However, due to the presence of the coating, the insulated coating wire and the electrode in the sensor need to be bonded after the coating of a distal end of the insulated coating wire is stripped, and the bonding is difficult.

Also in wiring to electrodes of products (devices) in semiconductor fields other than the fields of medical apparatus, insulated coating wires need to be bonded to the electrodes with high quality and high productivity. In the case of bonding the distal end of the insulated coating wire to an electrode in the device, the bonding needs to be performed after the coating is stripped similarly to the fields of medical apparatus.

The reasons why the bonding is performed after the coating is stripped as described above are as follows. If the distal end of an insulated coating wire is bonded to an electrode without stripping the coating of the distal end of the insulated coating wire, product failures such as low bonding strength between the electrode and the insulated coating wire and insufficient electric conduction therebetween may occur, and the stability as a product may be insufficient.

Conventionally, in view of the above, a method in which a coating at a distal end of an insulated coating wire is stripped in advance and the insulated coating wire is bonded to an electrode has been employed. For example, in semiconductor fields, as illustrated in FIG. 17, laser is applied to a distal end of an insulated coating wire 101 or the distal end of the insulated coating wire 101 is brought into contact with a heater to melt a coating such that a core (metal wire) 101*a* inside is exposed, and the core 101*a* is bonded to an electrode 102.

For example, a device is placed on a heater plate, and ultrasonic thermocompression bonding by heating is performed in some cases. By heating the device, an insulated coating of an insulated coating wire pressurized by a bonding tool is caused to flow, and removed from a bonding surface. By performing ultrasonic thermocompression bonding using heating as well, bonding quality is increased and time is reduced.

However, if the insulated coating is heated until the insulated coating becomes the flowing state (several hundreds of degrees or more), when a plurality of insulated coating wires are bonded, the first bonded insulated coating wire is continuously heated and the coating melts. If the heater temperature is too low, the insulated coating cannot be sufficiently removed, and a bonding failure occurs. In the case of a heat-sensitive device, the device cannot be heated sufficiently, and in the case of a device with high thermal capacity, heating and cooling require time, and productivity significantly decreases.

The above-mentioned method secure the bonding strength, but a laser or a heater dedicated for coating removal needs to be mounted on a device for bonding (see, for example, Patent Literature 1). Because these functions are provided, the size of the apparatus itself increases, and apparatus cost increases. Depending on the material of the coating, it may be difficult to remove the coating by heat of a heater. Damage to insulated coating wires by a step for applying heat for coating removal is also a concern.

If a coating of an insulated coating wire at a portion other than a bonding portion with an electrode is stripped, the insulated state cannot be maintained. Thus, advanced technologies for stably stripping a coating of the distal end of an insulated coating wire have been needed. Furthermore, it may be difficult to reliably electrically bond an electrode and a metal wire while preventing a coating of an insulated coating wire at a portion other than a bonding portion with the electrode from being stripped.

In the above-mentioned fields of medical apparatus, the work to strip a coating of the distal end of an insulated coating wire and the work to bond the distal end of the insulated coating wire and an electrode are manually performed in many cases. Thus, there is a problem in that the productivity significantly deteriorates and it is difficult to downsize products.

CITATION LIST

Patent Literature

Patent Literature 1: Japanese Patent Application Laid-open No. 2011-28923

SUMMARY OF INVENTION

Technical Problem

It is an object of one aspect of the present invention to provide a method for bonding an insulated coating wire capable of stably bonding a metal wire in an insulated coating wire to an electrode.

It is an object of one aspect of the present invention to provide a method for bonding an insulated coating wire, a connection structure, or a bonding apparatus capable of stripping a coating of an insulated coating wire and stably bonding the insulated coating wire to an electrode without using a laser or a heater.

It is an object of one aspect of the present invention to provide a method for stripping an insulated coating wire or a bonding apparatus capable of stably stripping a coating of an insulated coating wire at a bonding portion with an electrode.

Solution to Problem

Various aspects of the present invention are described below.

[1] A method for bonding an insulated coating wire for electrically connecting a first electrode and a second electrode to each other by an insulated coating wire in which a metal wire is coated with an organic substance, the method including:

a step (a) for placing the insulated coating wire onto the first electrode;

a step (b) for exposing a metal wire from the insulated coating wire; and a step (C) for forming a first bump over the exposed metal wire and the first electrode to electrically connect the metal wire to the first electrode.

[2] The method for bonding an insulated coating wire according to item [1], in which the step (b) includes pushing the insulated coating wire against the first electrode by a distal end of a tool to expose the metal wire from the insulated coating wire.

[3] The method for bonding an insulated coating wire according to item [2], in which the step (b) includes using a bonding apparatus including an ultrasonic horn and an ultrasonic transducer for supplying ultrasonic waves to the ultrasonic horn to hold the tool by the ultrasonic horn, and applying ultrasonic vibration to the tool to expose the metal wire from the insulated coating wire, and the step (C) includes using the bonding apparatus to hold a capillary through which a wire is inserted by the ultrasonic horn, applying a high voltage between a distal end of the wire protruding from a distal end of the capillary and a discharge electrode to cause discharge, and melting a distal end portion of the wire by discharge energy thereof to form the first bump.

[4] The method for bonding an insulated coating wire according to any one of items [1] to [3], in which the step (a) includes placing an insulated coating wire fed from a distal end of a capillary in a bonding apparatus onto a first position, and moving the capillary to a second position while feeding the insulated coating wire from the distal end of the capillary, to place the insulated coating wire onto the first electrode.

[5] The method for bonding an insulated coating wire according to any one of items [1] to [3], comprising, before the step (a):

a step for placing an insulated coating wire fed from a distal end of a capillary in a bonding apparatus onto a second electrode, and pushing the insulated coating wire against the second electrode by a distal end of a tool to expose the metal wire from the insulated coating wire; and a step for forming a second bump over the exposed metal wire and the second electrode to electrically connect the metal wire to the second electrode, wherein the step (a) includes moving the capillary while feeding the insulated coating wire from the distal end of the capillary to place the insulated coating wire onto the first electrode.

[6] The method for bonding an insulated coating wire according to item [1], wherein the step (a) includes pushing the insulated coating wire fed from a distal end of a capillary in a bonding apparatus against the first electrode with a pressurizing force, and the step (b) includes detecting that the capillary and the first electrode become a conductive state through a metal wire in the insulated coating wire at an adhesion portion between the insulated coating wire and the first electrode due to ultrasonic vibration of an ultrasonic horn in the bonding apparatus, and thereafter causing a current to flow between the capillary and the first electrode to heat the metal wire at the adhesion portion, thereby moving the insulated coating to outside of the adhesion portion and stripping the insulated coating from the insulated coating wire.

[7] A method for striping an insulated coating wire, comprising:

a step (a) for pushing an insulated coating wire fed from a distal end of a capillary in a bonding apparatus against a first electrode by pressurization;

a step (b) for detecting that the capillary and the first electrode become a conductive state through a metal wire in the insulated coating wire at an adhesion portion between the insulated coating wire and the first electrode due to ultrasonic vibration of an ultrasonic horn in the bonding apparatus; and a step (c) for causing a current to flow between the capillary and the first electrode to heat the metal wire at the adhesion portion, thereby moving the insulated coating to outside of the adhesion portion and stripping the insulated coating from the insulated coating wire.

[8] A method for bonding an insulated coating wire, comprising, after the insulated coating in the insulated coating wire is stripped by using the method for stripping an insulated coating wire according to item [7], a step (d) for causing a current to flow between the metal wire and the first electrode at the adhesion portion, and controlling the ultrasonic horn to perform ultrasonic vibration to apply ultrasonic vibration to the metal wire and the first electrode through the capillary, thereby electrically connecting the metal wire to the first electrode.

[9] A method for bonding an insulated coating wire, comprising:

a step (c) for pushing, at an adhesion portion between an insulated coating wire fed from a distal end of a capillary in a bonding apparatus and a first electrode, a metal wire exposed while an insulated coating of the insulated coating wire is stripped against the first electrode by the capillary; and a step (d) for causing a current to flow between the capillary and the first electrode and causing a current to flow between the metal wire and the first electrode at the adhesion portion, and controlling an ultrasonic horn in the bonding apparatus to perform ultrasonic vibration to apply ultrasonic vibration to the metal wire and the first electrode through the capillary, thereby electrically connecting the metal wire to the first electrode.

[10] The method for bonding an insulated coating wire according to item [8] or [9], comprising, after the step (d), a step (e) for stopping the ultrasonic vibration, and causing a current between the metal wire and the first electrode while pressurizing the metal wire at the adhesion portion against the first electrode by the capillary, thereby growing an alloy layer of the metal wire and the first electrode to enhance bonding strength.

[11] The method for bonding an insulated coating wire according to any one of items [8] to [10], comprising, after the step (d) or the step (e), a step (f) for forming a bump over the metal wire and the first electrode to electrically connect the metal wire to the first electrode by the bump.

[12] A connection structure, comprising:

a first electrode;

an insulated coating wire disposed on the first electrode, in which a metal wire is coated with an organic substance; and a first bump formed over the insulated coating wire and the first electrode, wherein a metal wire exposed from the insulated coating wire located on the first electrode and the first electrode are electrically connected by the first bump.

[13] The connection structure according to item [12], wherein one end of the insulated coating wire is coated with the organic substance; and the metal wire exposed from the insulated coating wire is located closer to another end of the insulated coating wire than the one end.

[14] The connection structure according to item [12] or [13], comprising:

a second electrode;

the insulated coating wire disposed on the second electrode; and a second bump formed on the insulated coating wire and the second electrode, wherein a metal wire exposed from the insulated coating wire located on the second electrode and the second electrode are electrically connected by the second bump.

[15] A connection structure, comprising:

a first electrode; and an insulated coating wire disposed on the first electrode, in which a metal wire is coated with an organic substance, wherein a metal wire exposed from the insulated coating wire located on the first electrode and the first electrode are bonded by an alloy layer grown between the metal wire and the first electrode.

[16] The connection structure according to any one of items [12] to [15], comprising a substrate on which the first electrode is disposed, wherein the substrate is a substrate of an electronic part used in a medical field.

[17] A bonding apparatus, comprising:

a capillary having conductivity for feeding an insulated coating wire;

an ultrasonic horn for holding the capillary;

a mechanism for vertically moving the capillary held by the ultrasonic horn;

an ultrasonic transducer for applying ultrasonic vibration to the ultrasonic horn;

an ultrasonic generator for controlling the ultrasonic transducer to oscillate ultrasonic waves;

a current source for causing a current to flow between a first electrode that bonds a metal wire in the insulated coating wire and the capillary through the metal wire;

a resistance detector for detecting a resistance value between the electrode and the metal wire, and the capillary; and a control unit for controlling the mechanism, the ultrasonic generator, the current source, and the resistance detector.

[18] The bonding apparatus according to item [17], wherein the control unit controls the mechanism to pressurize and push the insulated coating wire fed from a distal end of the capillary against the electrode, controls the ultrasonic generator to cause the ultrasonic horn to perform ultrasonic vibration, and controls the resistance detector to detect that the capillary and the first electrode become a conductive state through a metal wire in the insulated coating wire at an adhesion portion between the insulated coating wire and the first electrode, and thereafter controls the current source to cause a current to flow between the capillary and the first electrode to heat the metal wire at the adhesion portion to strip the insulated coating of the insulated coating wire.

[19] The bonding apparatus according to item [18], wherein, after stripping the insulated coating of the insulated coating wire, the control unit controls the current source to cause a current to flow between the metal wire and the first electrode at the adhesion portion, and controls the ultrasonic generator to cause the ultrasonic horn to perform ultrasonic vibration to apply ultrasonic vibration to the metal wire and the first electrode through the capillary, thereby electrically connecting the metal wire to the first electrode.

Advantageous Effects of Invention

One aspect of the present invention can provide a method for bonding an insulated coating wire capable of stably bonding a metal wire in an insulated coating wire and an electrode.

One aspect of the present invention can provide a method for bonding an insulated coating wire, a connection structure, or a bonding apparatus capable of stripping a coating of an insulated coating wire and stably bonding the insulated coating wire to an electrode without using a laser or a heater.

One aspect of the present invention can provide a method for stripping an insulated coating wire or a bonding apparatus capable of stably stripping a coating of an insulated coating wire at a bonding portion with an electrode.

Note that the "bonding apparatus" as used herein includes various bonding apparatus to which the present invention can be applied.

BRIEF DESCRIPTION OF DRAWINGS

FIGS. 5(A) to 5(C) are perspective views illustrating specific examples of a dedicated tool illustrated in FIG. 2.

FIG. 6 is a side view illustrating an example of a state in which a distal end of an insulated coating wire is bonded to an electrode by a bump.

FIGS. 14(A)-14(K) are schematic views for describing operation of the wire bonding apparatus illustrated in FIG. 13 in detail.

DESCRIPTION OF EMBODIMENTS

Embodiments of the present invention are described in detail below with reference to the drawings. However, the present invention is not limited to the following description, and it should be easily understood by a person skilled in the art that modes and details of the present invention can be variously modified without departing from the gist and scope of the present invention. Thus, the present invention is not intended to be interpreted as being limited to the description of the embodiments below.

First Embodiment

FIG. 1 to FIG. 4 are views for describing a method for bonding an insulated coating wire according to one aspect of the present invention.

Figure 1A:
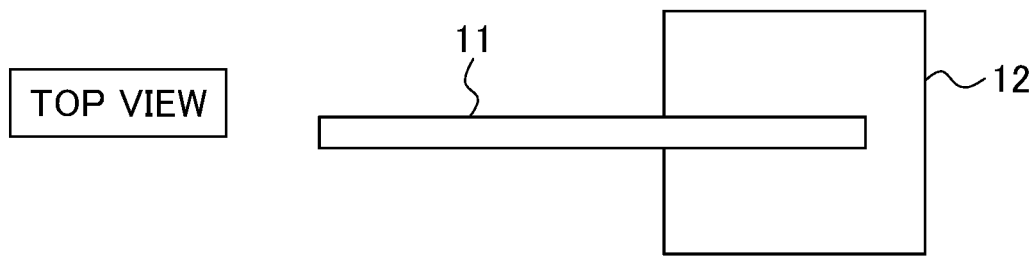
FIG. 1(A) is a top view for describing a method for bonding an insulated coating wire according to one aspect of the present invention.
Figure 1B:
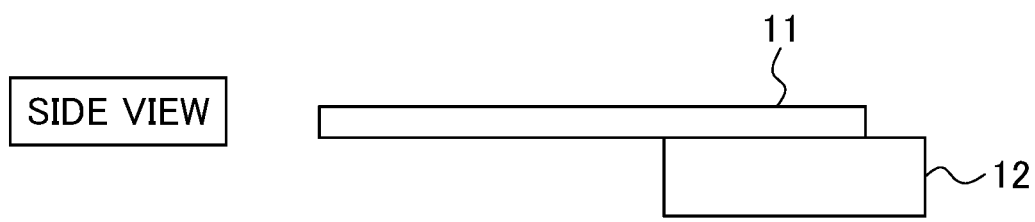
FIG. 1(B) is a side view for describing the method for bonding an insulated coating wire according to one aspect of the present invention.

First, as illustrated in FIGS. 1(A) and 1(B), an insulated coating wire 11 with unstripped coating is placed or set on an electrode (also referred to as "first electrode") 12 of an electronic part or a substrate. This operation may be performed manually or by a machine. Note that the insulated coating wire 11 is an insulated coating wire in which a metal wire is coated with an organic substance. The material of the metal wire is gold, silver, copper, platinum, stainless steel, tungsten, rhodium, or iridium. The material of the organic substance is a polyamide-based material (for example, polyamide or polyamide imide), a polyester-based material (for example, polyester or polyester imide), polyimide, polyethylene, polypropylene, vinyl chloride, or a fluorine-based resin material (for example, FEP, ETFE, PFA, PVDF, PTFE, or PCTFE). The substrate includes a substrate used in medical fields, such as an electronic part, and a substrate used in semiconductor fields other than medical fields. Examples of the electronic part used in medical fields include a self-contained sensor and a self-contained BMI apparatus.

Figure 2:
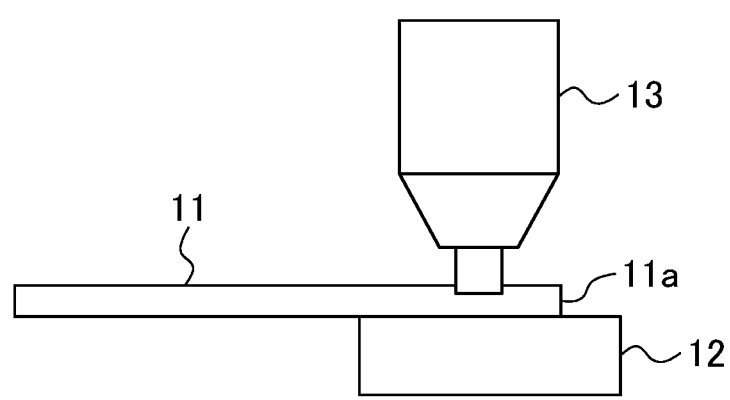
FIG. 2 is a side diagram for describing the method for bonding an insulated coating wire according to one aspect of the present invention.

Next, as illustrated in FIG. 2, the other end side of the insulated coating wire 11 with respect to one end 11a is pushed against the electrode 12 by a distal end of a dedicated tool 13, and the dedicated tool 13 is moved backward and forward to strip the coating. As another method, an ultrasonic horn (not shown) is mounted to an upper part (not shown) of the dedicated tool 13 such that ultrasonic vibration can be applied, and the coating may be stripped by ultrasonic vibration. A coating surface is stripped due to the effect that a part of the coating surface is applied with heat and melted by the ultrasonic vibration and the effect that the coating surface is stripped by the distal end of the dedicated tool.

Figure 3A:
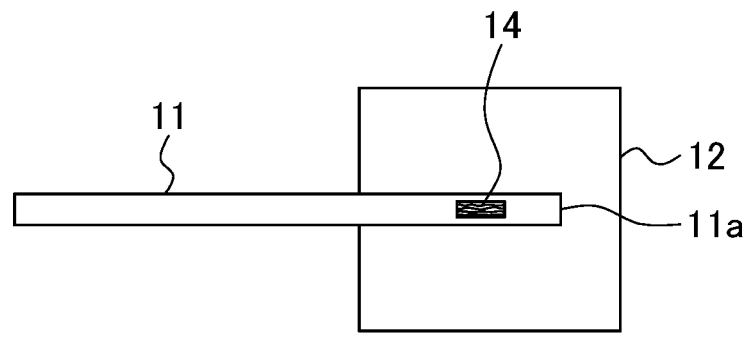
FIG. 3(A) is a top view for describing the method for bonding an insulated coating wire according to one aspect of the present invention.
Figure 3B:
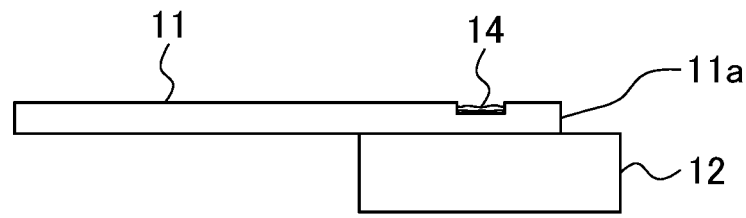
FIG. 3(B) is a side view for describing the method for bonding an insulated coating wire according to one aspect of the present invention.

After that, the distal end of the dedicated tool 13 is detached from the insulated coating wire 11. In this manner, as illustrated in FIGS. 3(A) and 3(B), the coating of the insulated coating wire 11 is stripped, and a metal wire 14 on the other end side of the insulated coating wire 11 with respect to one end 11a is exposed. In this case, the insulated coating wire 11 becomes "temporarily fixed state" in which the insulated coating wire 11 is bonded to the electrode 12 with weak force. A slight crack occurs in the surface of the insulated coating wire 11, and the metal wire (core) 14 in the insulated coating wire 11 is exposed.

The step illustrated in FIG. 2 is performed by using a wire bonding apparatus (not shown) in which a capillary is replaced with the dedicated tool 13. In other words, as the dedicated tool 13, a tamping tool for crimping the top surface of the insulated coating wire 11 placed on the electrode 12 may be used instead of a capillary (tool used by inserting wire therethrough) used in an ordinary wire bonding apparatus. Note that a tool made of metal or ceramics may be used as the dedicated tool 13. As the wire bonding apparatus, a publicly known wire bonding apparatus may be used. For example, the wire bonding apparatus includes an ultrasonic horn, and an ultrasonic transducer for supplying ultrasonic waves to the ultrasonic horn. The dedicated tool 13 is held by the ultrasonic horn, and ultrasonic vibration is applied to the dedicated tool 13, so that the metal wire 14 can be exposed from the insulated coating wire 11.

The distal end of the dedicated tool 13 only needs to have a shape capable of exposing the metal wire 14 from the insulated coating wire 11, and various shapes can be used. Various shapes can be used depending on the materials and dimensions of the insulated coating wire and the electrode. As specific examples, a distal end 10a of a dedicated tool 13a may have a mesh portion (plurality of pointed portions) as illustrated in FIG. 5(A), a distal end 10b of a dedicated tool 13b may have a cross-shaped portion as illustrated in FIG. 5(B), and a distal end 10 of a dedicated tool 13 may have a square portion as illustrated in FIG. 5(C). Note that, in the present embodiment, the dedicated tool 13 illustrated in FIG. 5(C) is used.

Figure 4A:
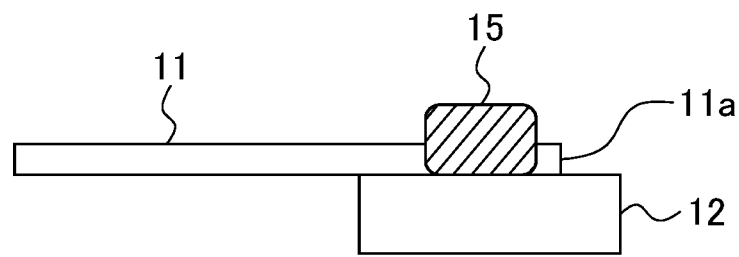
FIG. 4(A) is a top view for describing the method for bonding an insulated coating wire according to one aspect of the present invention.
Figure 4B:
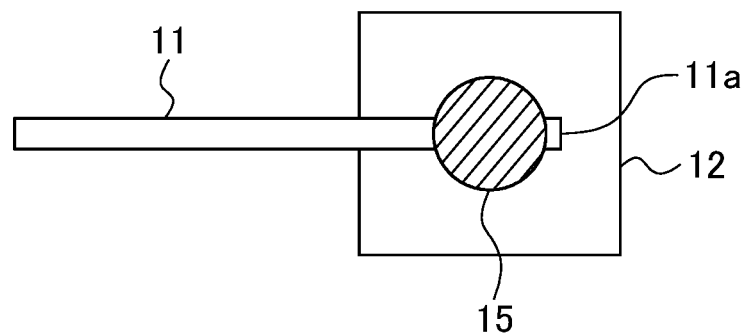
FIG. 4(B) is a side view for describing the method for bonding an insulated coating wire according to one aspect of the present invention.

After that, a wire bonding apparatus (not shown) is used to hold a capillary through which a wire made of metal, such as gold, silver, copper, and platinum, by the ultrasonic horn, and the wire is fed from the capillary. A high voltage is applied between a distal end of the wire protruding from a distal end of the capillary and a discharge electrode to cause spark discharge. A distal end portion of the wire is melted by discharge energy thereof to create a ball. The ball is pushed onto the insulated coating wire 11 temporarily fixed on the electrode 12 illustrated in FIG. 3 to disconnect the wire. In this manner, as illustrated in FIGS. 4(A) and 4(B), the insulated coating wire 11 from which the metal wire 14 is exposed and the electrode 12 are directly bonded by a bump (also referred to as "first bump") 15. By using the bump 15 formed from the ball made of metal, even when the contact portion between the insulated coating wire 11 and the electrode 12 is insulated, if a slight crack has occurred in the coating, electric conduction between the metal wire 14 exposed therefrom and the electrode 12 can be secured. In addition thereto, the bonding strength between the insulated coating wire 11 and the electrode 12 can be increased to maintain the stable bonding state, and stable electric conduction can be secured. Note that the material of the bump 15 is gold, silver, copper, or platinum.

In the thus obtained connection structure illustrated in FIGS. 4(A) and 4(B), the bump 15 is formed on the insulated coating wire 11 and the electrode 12, and the metal wire 14 exposed from the insulated coating wire 11 located on the electrode 12 and the electrode 12 are electrically connected by the bump 15. One end 11a of the insulated coating wire 11 is coated with an organic substance, and the metal wire exposed from the other end side of the insulated coating wire 11 with respect to one end 11a and the electrode 12 are electrically connected by the bump 15.

Note that, as the wire bonding apparatus for forming the bump 15 illustrated in FIG. 4, the same apparatus as the wire bonding apparatus used in the step illustrated in FIG. 2 may be used, and a different apparatus may be used. For example, by changing a tool mounted to the wire bonding apparatus from a capillary, the operations at the bump formation step illustrated in FIG. 4 and the step illustrated in FIG. 2 can be performed by the same wire bonding apparatus.

In the present embodiment, one end 11a of the insulated coating wire 11 is exposed from the bump 15 that bonds the insulated coating wire 11 and the electrode 12 as illustrated in FIG. 4, but as illustrated in FIG. 6, the distal end of the insulated coating wire 11 is not necessarily required to be exposed from the bump 15 that bonds the insulated coating wire 11 and the electrode 12.

In the bonding method illustrated in FIG. 6, without using a dedicated jig, a capillary in an ordinary wire bonding apparatus is used to push the insulated coating wire 11 against the electrode and tear the insulated coating wire 11, and the coating of the distal end of the insulated coating wire 11 is stripped to expose a metal wire at the distal end of the insulated coating wire 11. The distal end of the insulated coating wire 11 and the electrode 12 may be directly bonded by a bump 15, so that the distal end of the insulated coating wire 11 is not exposed from the bump 15.

The formation method for the bump 15 is the same as the formation method for the bump 15 illustrated in FIG. 4. Specifically, a wire to be inserted through the capillary is replaced from an insulated coating wire with a metal wire such as gold, silver, copper, and platinum, and discharge is applied to the wire to create a ball. The ball is pushed onto the insulated coating wire 11 to disconnect the wire. In this manner, the same bonding as the bonding in FIG. 4 can be performed (see FIG. 6).

This method has an advantage in that bonding can be performed without using a dedicated jig because a capillary in a wire bonding apparatus is used.

According to the present embodiment, the coating of the insulated coating wire 11 can be peeled and the insulated coating wire 11 can be stably bonded to the electrode 12 without using a laser or a heater. In other words, all operations can be performed by replacing a bonding tool in a wire bonding apparatus, and hence the coating of the insulated coating wire 11 can be stripped and the insulated coating wire 11 can be stably bonded to the electrode 12 without requiring a complicated mechanical structure for stripping a coating, such as a laser unit or a heater unit.

A step for stripping the coating is not necessary before bonding, and hence the operation can be simplified and the speed of the operation can be increased.

Even when the coating is not completely removed, by bonding the electrode 12 and the insulated coating wire 11 through the bump 15 made of metal, both the electric conduction and the bonding strength between the metal wire 14 and the electrode 12 can be secured, leading to the stability of products.

The coating is not removed more than necessary, and hence if the bonding method is used for products used in fields of medical apparatus, the influence on human bodies can be reduced. Works that have been manually performed can be automated by machines, and hence the productivity and the quality can be improved, the variation in product quality can be suppressed, and the products can be downsized.

Second Embodiment

Figure 7A:
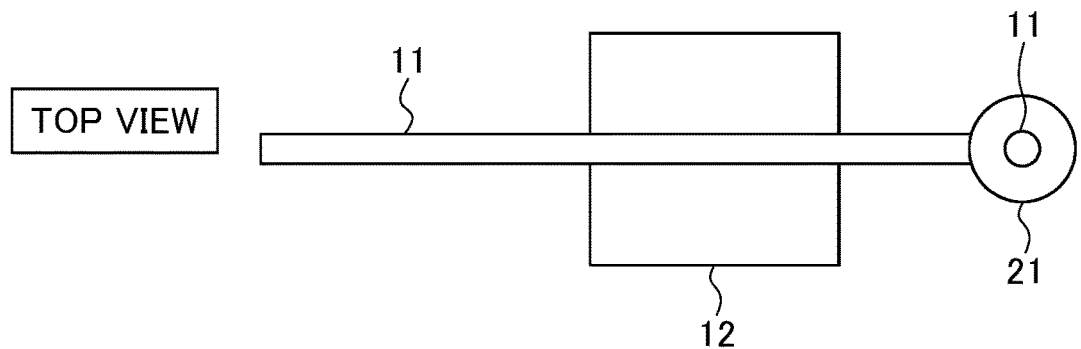
FIG. 7(A) is a top view for describing the method for bonding an insulated coating wire according to one aspect of the present invention.
Figure 7B:
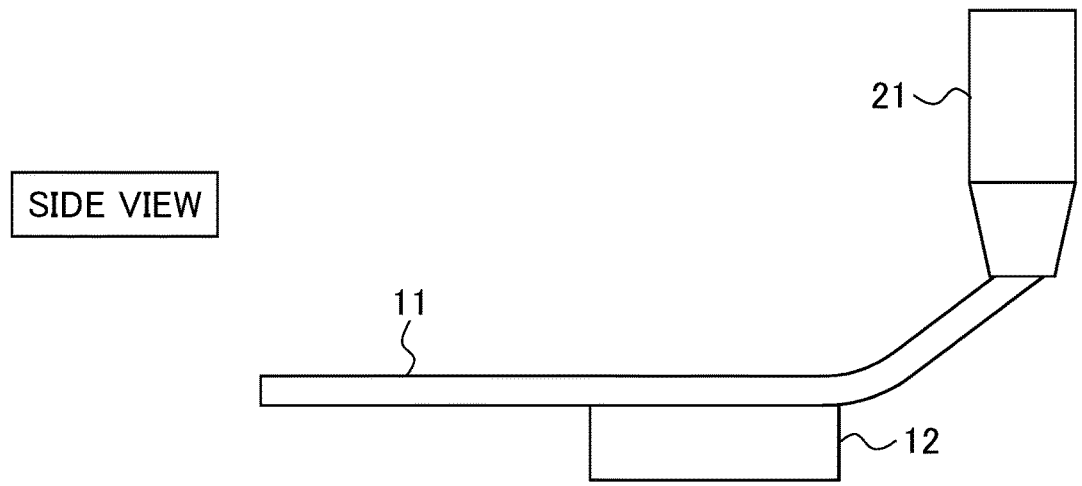
FIG. 7(B) is a side view for describing the method for bonding an insulated coating wire according to one aspect of the present invention.
Figure 8:
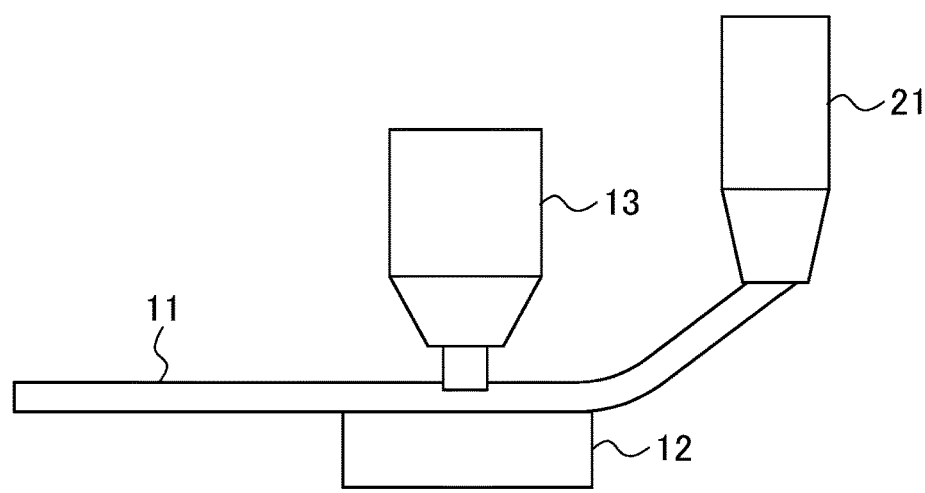
FIG. 8 is a side view for describing the method for bonding an insulated coating wire according to one aspect of the present invention.

FIG. 7 and FIG. 8 are diagrams for describing a method for bonding an insulated coating wire according to one aspect of the present invention. The same parts as in FIG. 1 to FIG. 4 are denoted by the same reference symbols.

First, as illustrated in FIGS. 7(A) and 7(B), an insulated coating wire 11 fed from a distal end of a capillary 21 in a wire bonding apparatus (not shown) is placed or fixed at a first position, and the capillary 21 is moved to a second position while feeding the insulated coating wire 11 from the distal end of the capillary 21, so that the insulated coating wire 11 with coating stripped is placed on a first electrode 12 of an electronic part.

Next, as illustrated in FIG. 8, the insulated coating wire 11 is pushed against the first electrode 12 by a distal end of a dedicated tool 13.

Although a subsequent step is not illustrated, the distal end of the dedicated tool 13 is detached from the insulated coating wire 11. In this manner, the coating of the insulated coating wire 11 is peeled, and a metal wire in the insulated coating wire 11 is exposed. In this case, the insulated coating wire 11 becomes "temporarily fixed state" in which the insulated coating wire 11 is bonded to the first electrode 12 with weak force. A slight crack occurs in the surface of the insulated coating wire 11, and a metal wire (core) in the insulated coating wire 11 is exposed.

After that, a ball created by using a wire made of metal such as gold, silver, copper, and platinum by a wire bonding apparatus (not shown) is pushed onto the insulated coating wire temporarily fixed on the first electrode 12, and the insulated coating wire 11 from which the metal wire is exposed and the first electrode 12 are directly bonded by a bump.

After that, a metal wire exposed on the end portion side of the insulated coating wire 11 placed or fixed at the above-mentioned first position and a second electrode may be bonded by a bump (not shown).

Also in the present embodiment, the same effects as in the first embodiment can be obtained.

Third Embodiment

Figure 9A:
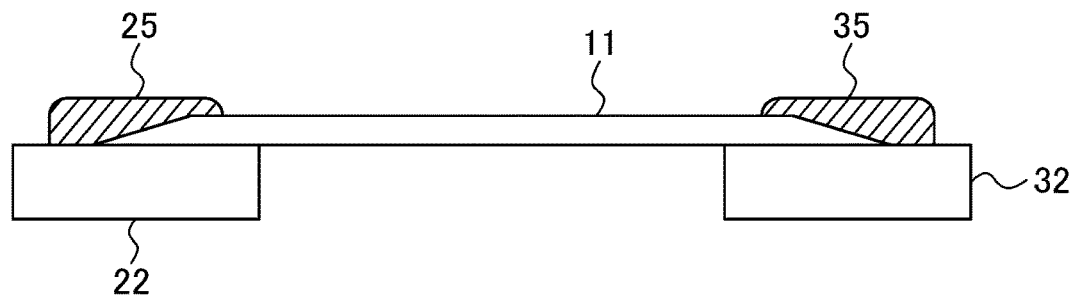
FIG. 9(A) is a view for describing the method for bonding an insulated coating wire according to one aspect of the present invention.

FIG. 9(A) is a diagram for describing a method for bonding an insulated coating wire according to one aspect of the present invention.

First, an insulated coating wire 11 fed from a distal end of a capillary (not shown) in a wire bonding apparatus (not shown) is placed or fixed onto a first electrode (also referred to as "second electrode") 22 of an electronic part.

Next, the insulated coating wire 11 is pushed against the first electrode 22 by the distal end 10 of the dedicated tool 13 illustrated in FIG. 5(C), and the distal end of the dedicated tool 13 is detached from the insulated coating wire 11, so that a metal wire is exposed from the insulated coating wire 11, and the insulated coating wire 11 is temporarily fixed onto the first electrode 22.

After that, a ball created by using a wire made of metal by the wire bonding apparatus (not shown) is pushed onto the insulated coating wire 11 temporarily fixed on the first electrode 22, and the insulated coating wire 11 from which the metal wire is exposed and the first electrode 22 are directly bonded by a first bump (also referred to as "second bump") 25. In this manner, the metal wire in the insulated coating wire 11 is electrically connected to the first electrode 22.

Next, the capillary is moved onto a second electrode (also referred to as "first electrode") 32 while feeding the insulated coating wire 11 from the distal end of the capillary, thereby placing or fixing the insulated coating wire 11 onto the second electrode 32.

Next, the insulated coating wire 11 is pushed against the second electrode 32 by the distal end 10 of the dedicated tool 13 illustrated in FIG. 5(C), and the distal end of the dedicated tool 13 is detached from the insulated coating wire 11, so that a metal wire is exposed from the insulated coating wire 11, and the insulated coating wire 11 is temporarily fixed onto the second electrode 32.

After that, a ball created by using a wire made of metal by the wire bonding apparatus (not shown) is pushed onto the insulated coating wire 11 temporarily fixed on the second electrode 32, and the insulated coating wire 11 from which the metal wire is exposed and the second electrode 32 are directly bonded by a second bump (also referred to as "first bump") 35. In this manner, the metal wire in the insulated coating wire 11 is electrically connected to the second electrode 32.

The thus obtained connection structure illustrated in FIG. 9(A) is as follows. One end of the insulated coating wire 11 is disposed on the first electrode 22, and the first bump 25 is formed on one end of the insulated coating wire 11 and the first electrode 22. The metal wire exposed from the insulated coating wire 11 located on the first electrode 22 is electrically connected to the first electrode 22 by the first bump 25. The other end of the insulated coating wire 11 is disposed on the second electrode 32, and the second bump 35 is formed on the other end of the insulated coating wire 11 and the second electrode 32. The metal wire exposed from the insulated coating wire 11 located on the second electrode 32 is electrically connected to the second electrode 32 by the second bump 35.

Also in the present embodiment, the same effects as in the first embodiment can be obtained.

Note that, in the present embodiment, the capillary in the wire bonding apparatus is used to place or fix the insulated coating wire 11 onto the first electrode 22 or place or fix the insulated coating wire 11 onto the second electrode 32, but the placement or the fixation may be manually performed.

Figure 9B:
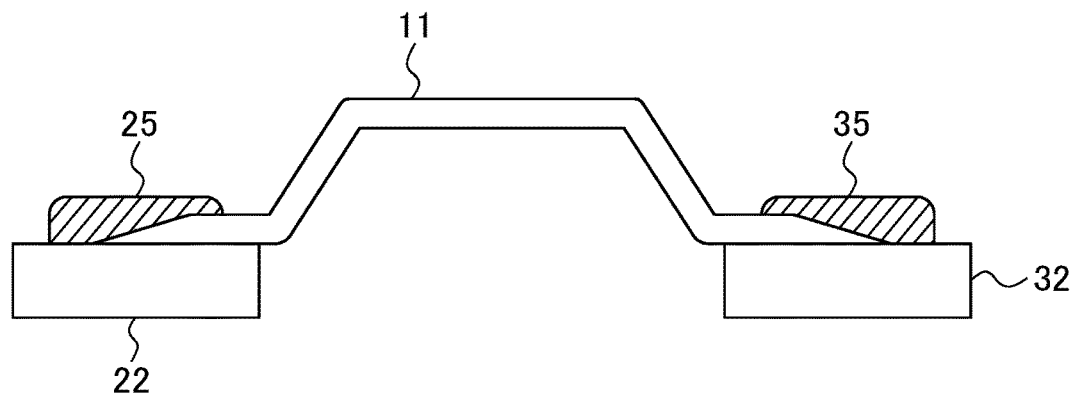
FIG. 9(B) is a view illustrating a modification of a bonding state of an insulated coating wire according to one aspect of the present invention.

In the present embodiment, the insulated coating wire 11 between the first electrode 22 and the second electrode 32 has a linear shape as illustrated in FIG. 9(A), but the shape is not limited thereto. As illustrated in FIG. 9(B), the insulated coating wire 11 between the first electrode 22 and the second electrode 32 may have a loop shape.

Fourth Embodiment

Figure 10:
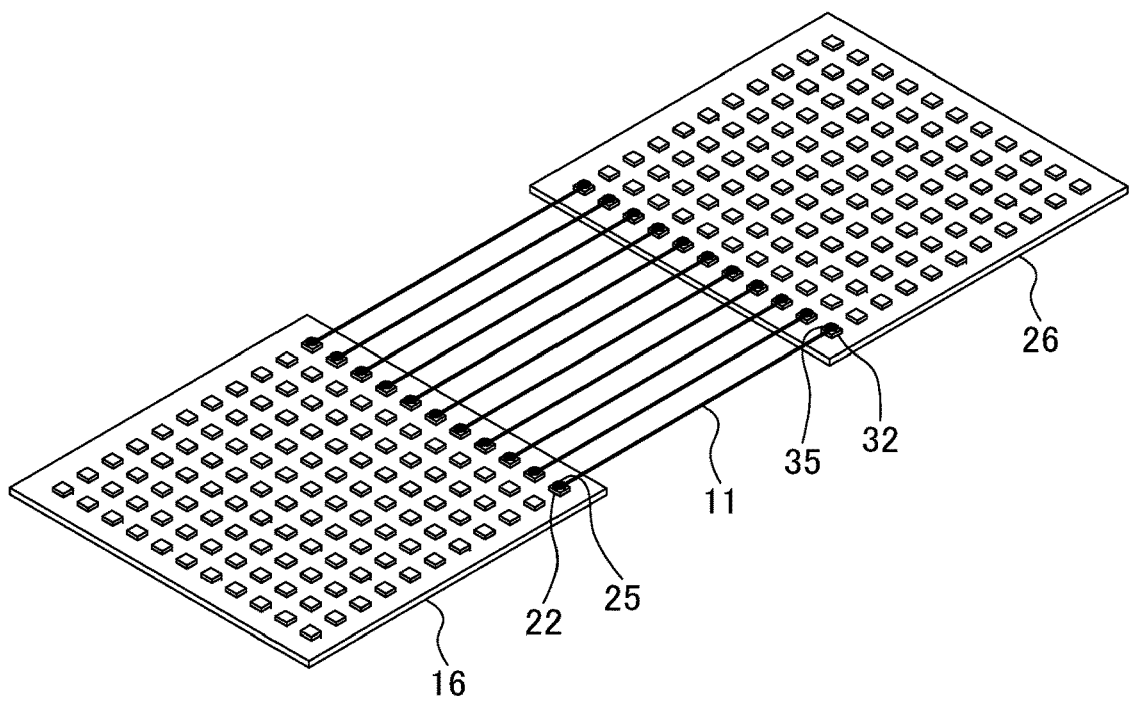
FIG. 10 is a perspective view illustrating a substrate of an electronic part used in medical fields according to one aspect of the present invention.

FIG. 10 is a perspective view illustrating a substrate of an electronic part used in medical fields according to one aspect of the present invention.

The substrate of this medical product includes a first substrate 16 and a second substrate 26, in which a plurality of first electrodes 22 are disposed on the first substrate 16 and a plurality of second electrodes 32 are disposed on the second substrate 26. Each of the first electrodes 22 and the second electrodes 32 is a bonding pad.

The first electrodes 22 and the second electrodes 32 are electrically connected by insulated coating wires 11 and first and second bumps 25 and 35. Note that the same connection method and the same connection structure for the first electrode 22 and the second electrode 32 as those in any of the first to third embodiments can be used.

Also in the present embodiment, the same effects as in the first embodiment can be obtained.

Fifth Embodiment

Figure 11:
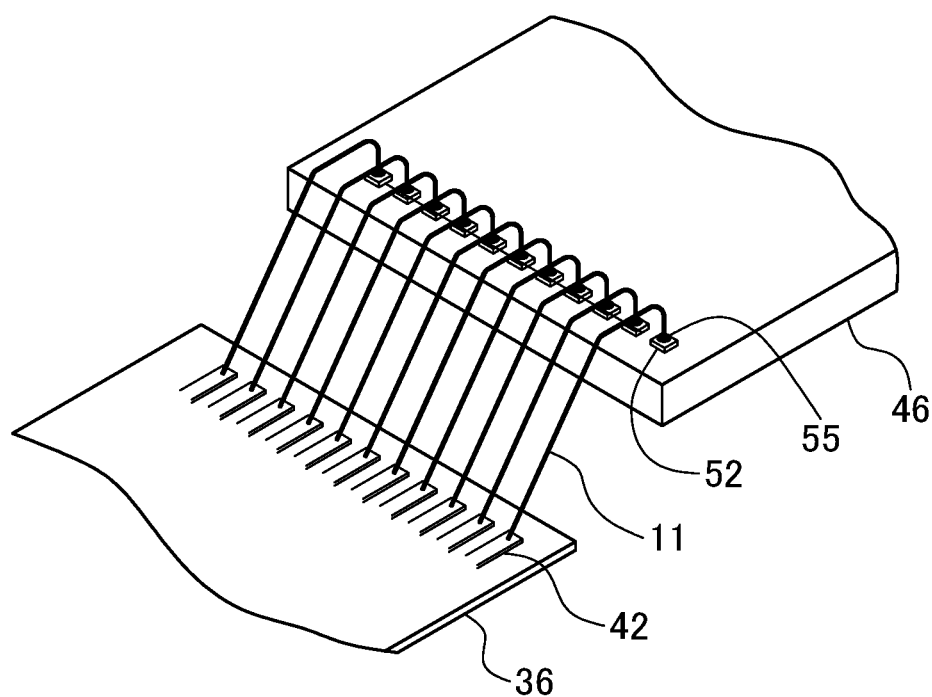
FIG. 11 is a perspective view illustrating a substrate used in semiconductor fields according to one aspect of the present invention.

FIG. 11 is a perspective view illustrating a substrate used in semiconductor fields according to one aspect of the present invention. A semiconductor product refers to an electronic part used in semiconductor fields.

The substrate of this semiconductor product includes a first substrate 36 and a second substrate 46, in which a plurality of first electrodes 42 are disposed on the first substrate 36 and a plurality of second electrodes 52 are disposed on the second substrate 46.

The first electrodes 42 and the second electrodes 52 are electrically connected by insulated coating wires 11, first bumps (not shown), and second bumps 55. Note that the same connection method and the same connection structure for the first electrode 42 and the second electrode 52 as those in any of the first to third embodiments can be used.

Also in the present embodiment, the same effects as in the first embodiment can be obtained.

Figure 12:
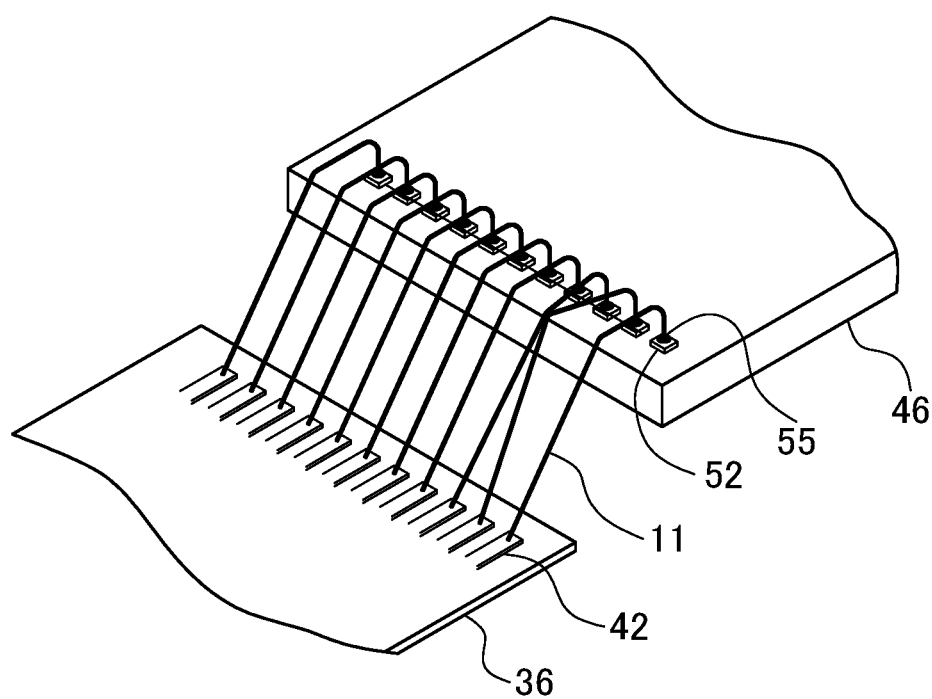
FIG. 12 is a perspective view for describing effects of a connection structure illustrated in FIG. 11.

The reason why the insulated coating wire 11 rather than an uncoated metal wire is used for electrical connection between the first electrode 42 and the second electrode 52 is that when the pitch between the electrodes is narrow, if the insulated coating wire 11 is slightly tilted as illustrated in FIG. 12, the insulated coating wire 11 may contact with an adjacent insulated coating wire 11. When the insulated coating wire 11 contacts an adjacent insulated coating wire 11 as described above, short-circuit occurs if uncoated metal wires are used. However, the insulation is maintained if the insulated coating wires 11 are used.

Sixth Embodiment

Figure 13:
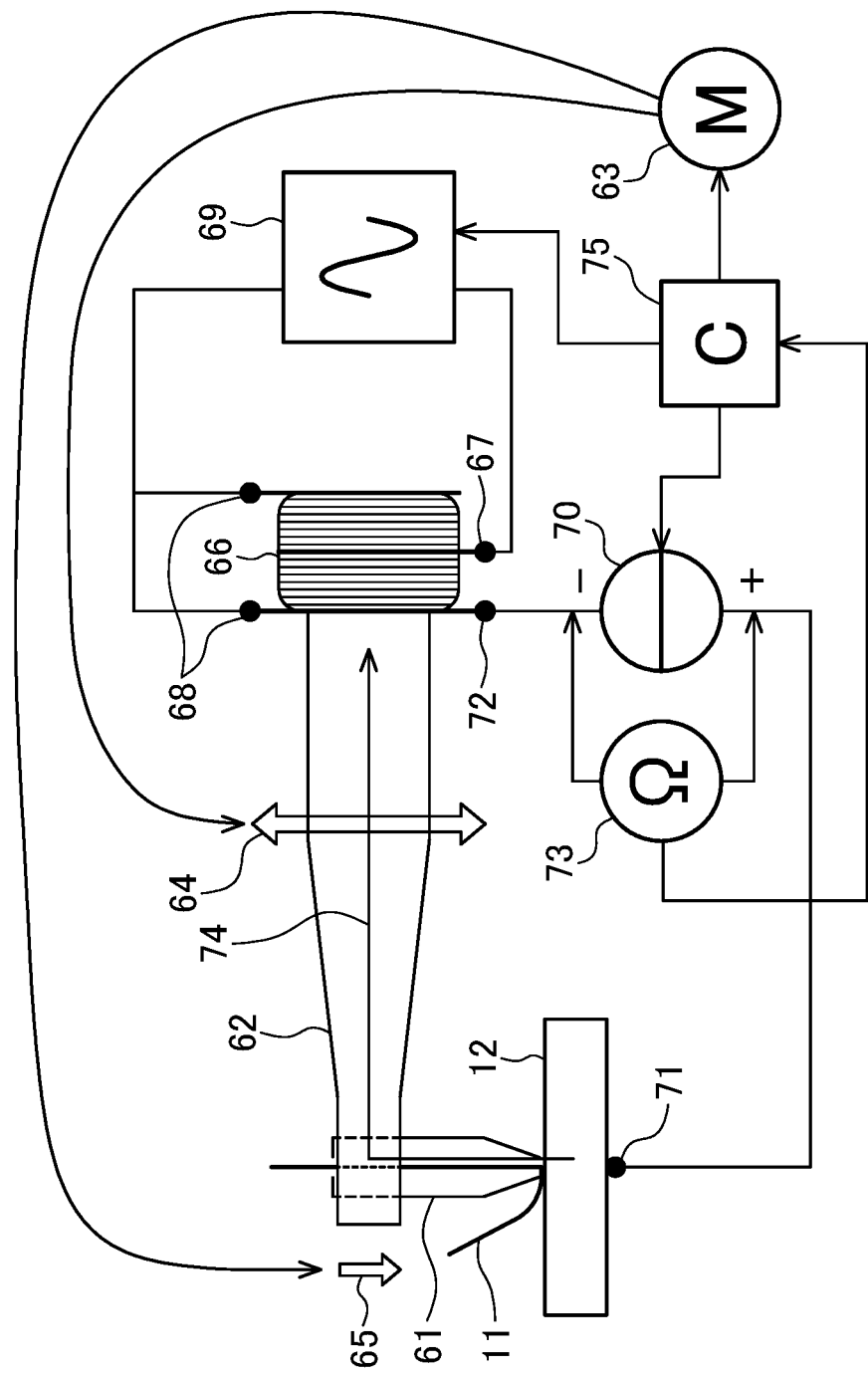
FIG. 13 is a view schematically illustrating a wire bonding apparatus according to one aspect of the present invention.

FIG. 13 is a view schematically illustrating a wire bonding apparatus according to one aspect of the present invention. The same parts as in FIG. 1 to FIG. 4 are denoted by the same reference symbols.

The wire bonding apparatus in FIG. 13 is an apparatus for bonding an insulated coating wire 11. The apparatus includes a capillary 61 as a bonding tool for feeding an insulated coating wire 11. The capillary 61 is formed from a hard material having conductivity, such as cemented carbide and cermet. A through hole for inserting the insulated coating wire 11 therethrough is formed at the center of the capillary 61.

The capillary 61 is fitted to a mounting hole at a distal end portion of an ultrasonic horn 62, and held by being fastened by a screw (not shown). The wire bonding apparatus includes a mechanism for vertically moving the capillary 61 held by the ultrasonic horn 62. This mechanism is a mechanism (not shown) using power of a motor 63. The mechanism enables the ultrasonic horn 62 to be vertically moved in a direction of an arrow 64. In this manner, the capillary 61 mounted to the ultrasonic horn 62 can be pushed against and separated from the first electrode 12. The above-mentioned mechanism enables the capillary 61 to be pushed against the first electrode 12 in a direction of an arrow 65 with a predetermined pressurizing force.

An ultrasonic transducer 66 for applying ultrasonic vibration is mounted to the ultrasonic horn 62, and an ultrasonic generator 69 for oscillating ultrasonic waves is connected to the ultrasonic transducer 66. Specifically, a transducer positive electrode 67 and transducer negative electrodes 68 are connected to the ultrasonic transducer 66, and the transducer positive electrode 67 and the transducer negative electrodes 68 are electrically connected to the ultrasonic generator 69. When a sine wave voltage is applied from the ultrasonic generator 69 to the transducer positive electrode 67 and the transducer negative electrodes 68, the ultrasonic transducer 66 is driven, and as a result, the ultrasonic transducer 66 performs ultrasonic vibration. Specifically, the vibration frequency of ultrasonic vibration is controlled to match with natural vibration of the ultrasonic horn 62, and the vibration amplitude is amplified by resonance of the ultrasonic horn 62. Then, ultrasonic vibration for mechanical processing can be applied to a distal end portion of the capillary 61.

The wire bonding apparatus includes a constant current source 70 for causing a current to flow between an electrode (also referred to as "first electrode") 12 that bonds a metal wire in the insulated coating wire 11 and the capillary 61 through the metal wire. The constant current source 70 has a current ON/OFF function and a current value variable function. An energization positive electrode 71 electrically connected to the first electrode 12 and an energization negative electrode common to the transducer negative electrode 68 are electrically connected to the constant current source 70. In this manner, a constant energization current can be caused to flow from the first electrode 12 to the metal wire in the insulated coating wire 11, the capillary 61, and the ultrasonic horn 62 as indicated by an arrow 74.

The wire bonding apparatus includes a resistance detector 73 for detecting a resistance value between the first electrode 12 and the metal wire in the insulated coating wire 11, and the capillary 61. The resistance detector 73 is electrically connected to both electrodes of the constant current source 70. The resistance detector 73 monitors a resistance value between the energization positive electrode 71 and the energization negative electrode 72, and functions to supply a current from the constant current source 70 when triggered by dielectric breakdown between both electrodes.

The wire bonding apparatus includes a controller 75 as a control unit for controlling a mechanism for moving the above-mentioned ultrasonic horn 62 in an arc pattern, the ultrasonic generator 69, the constant current source 70, and the resistance detector 73. When instructed by the controller 75, the ultrasonic transducer 66 can perform ultrasonic vibration by the ultrasonic generator 69. When instructed by the controller 75, the constant current source 70 can cause a current to flow from the first electrode 12 to the capillary 61. The resistance detector 73 notifies the controller 75 of dielectric breakdown between the first electrode 12 and the capillary 61. Furthermore, by controlling the motor 63 by the controller 75, the ultrasonic horn 62 can be vertically moved, and the capillary 61 can be moved as indicated by the arrow 65 to pressurize the insulated coating wire 11 onto the first electrode 12.

Next, a method for bonding an insulated coating wire is described while describing the operation of the above-mentioned wire bonding apparatus.

First, the insulated coating wire 11 fed from the distal end of the capillary 61 as a bonding tool is pushed against the first electrode 12 with predetermined pressurizing force. At this time, the insulated coating of the insulated coating wire is not broken, and electrical insulation between the capillary 61 having conductivity and the first electrode 12 similarly having conductivity is maintained. Next, by causing the ultrasonic horn 62 to perform ultrasonic vibration, high frequent repeated stress due to the ultrasonic vibration is applied to a contact point between the capillary 61 and the insulated coating wire 11 and an adhesion portion between the insulated coating wire 11 and the first electrode 12, and a crack occurs in the insulated coating at both contact points, with the result that partial breakdown occurs in the insulated coating. In this manner, the capillary 61 and the first electrode 12 become the conductive state through the metal wire (core) in the insulated coating wire 11 at the adhesion portion between the insulated coating wire 11 and the first electrode 12. The change from the insulated state to the conductive state is detected by the resistance detector 73 and transmitted to the controller 75.

After that, the controller 75 to which the conductive state has been transmitted from the resistance detector 73 instructs the constant current source 70 to start to cause a current set in advance to flow from the energization positive electrode 71 placed on the first electrode 12 to the energization negative electrode 72 placed on the ultrasonic horn 62. The resistance value from the energization positive electrode 71 to the first electrode 12 and the resistance value from the energization negative electrode 72 to the distal end of the capillary 61 are set to be as low as possible, and hence the resistance value at a contact portion between the capillary 61 and the metal wire (core) in the insulated coating wire 11 and the resistance value at a contact portion between the metal wire and the first electrode 12 with respect to the resistance values are high, and power loss concentrates. As a result, high Joule heat is locally generated, and heating is performed. In this manner, the insulated coating is moved to the outside of the adhesion portion between the insulated coating wire 11 and the first electrode 12 to strip the insulated coating from the insulated coating wire 11.

Specifically, due to the heating immediately after dielectric breakdown, an insulated coating formed from a thermoplastic organic substance around the bonding surface of the insulated coating wire 11 and the first electrode 12 becomes the flowing state. By applying appropriate pressure and ultrasonic vibration, the flowing insulated coating is pushed to the outer edge of the bonding surface without being distributed. Owing to mutual action of heat, pressure, and ultrasonic vibration, organic substances, oxides, and moisture, which hinder the bonding, are removed from the bonding surface, and a clean bonding surface is formed. In this manner, the insulated coating is stripped from the insulated coating wire 11.

Next, the energization current value, the ultrasonic vibration amplitude, and the pressurizing force are switched, and the flow proceeds to a bonding step. As an example, the energization current value is decreased, the ultrasonic vibration is increased, and the pressurizing force is gradually increased, thereby performing ultrasonic solid-phase bonding between the metal wire in the insulated coating wire 11 and the surface of the first electrode 12. In this manner, the metal wire in the insulated coating wire 11 is electrically connected to the first electrode 12.

After the bonding between the metal wire and the first electrode 12 is completed, the ultrasonic vibration is stopped, the pressurization is maintained, and the energization current is increased for a given period, thereby heating the bonding portion to grow an alloy layer between the metal wire and the first electrode 12 to achieve a more rigid bonding state. By controlling temperature and heating time by the energization current, the sizes of crystal grains can be controlled in a recrystallization process of the alloy layer and peripheral metal in the bonding surface to further improve the bonding strength.

Note that the present embodiment can be carried out while being modified as follows.

After an insulated coating is stripped from the insulated coating wire 11, the step illustrated in FIG. 4 is performed without performing ultrasonic solid-phase bonding between the metal wire in the insulated coating wire 11 and the surface of the first electrode 12 as described above. In other words, after an insulated coating is stripped from the insulated coating wire 11 by the above-mentioned method, the capillary 61 is moved from the first electrode 12, and a capillary (not shown) through which a wire made of metal such as gold, silver, copper, and platinum is inserted is held by another ultrasonic horn (not shown). The wire is fed from the capillary, and a high voltage is applied between a distal end of the wire protruding from the distal end of the capillary and a discharge electrode to cause spark discharge. A distal end portion of the wire is melted by discharge energy thereof to create a ball. The ball is pushed onto the insulated coating wire 11 temporarily fixed on the first electrode 12 to disconnect the wire. In this manner, the insulated coating wire 11 from which the metal wire is exposed and the first electrode 12 are directly bonded by a bump (not shown) (also referred to as "first bump").

After an alloy layer between the metal wire and the first electrode 12 is grown to achieve a more rigid bonding state as described above, a bump (not shown) over the metal wire and the first electrode 12 may be formed so that the metal wire is further electrically connected to the first electrode 12 by the bump.

Figure 15:
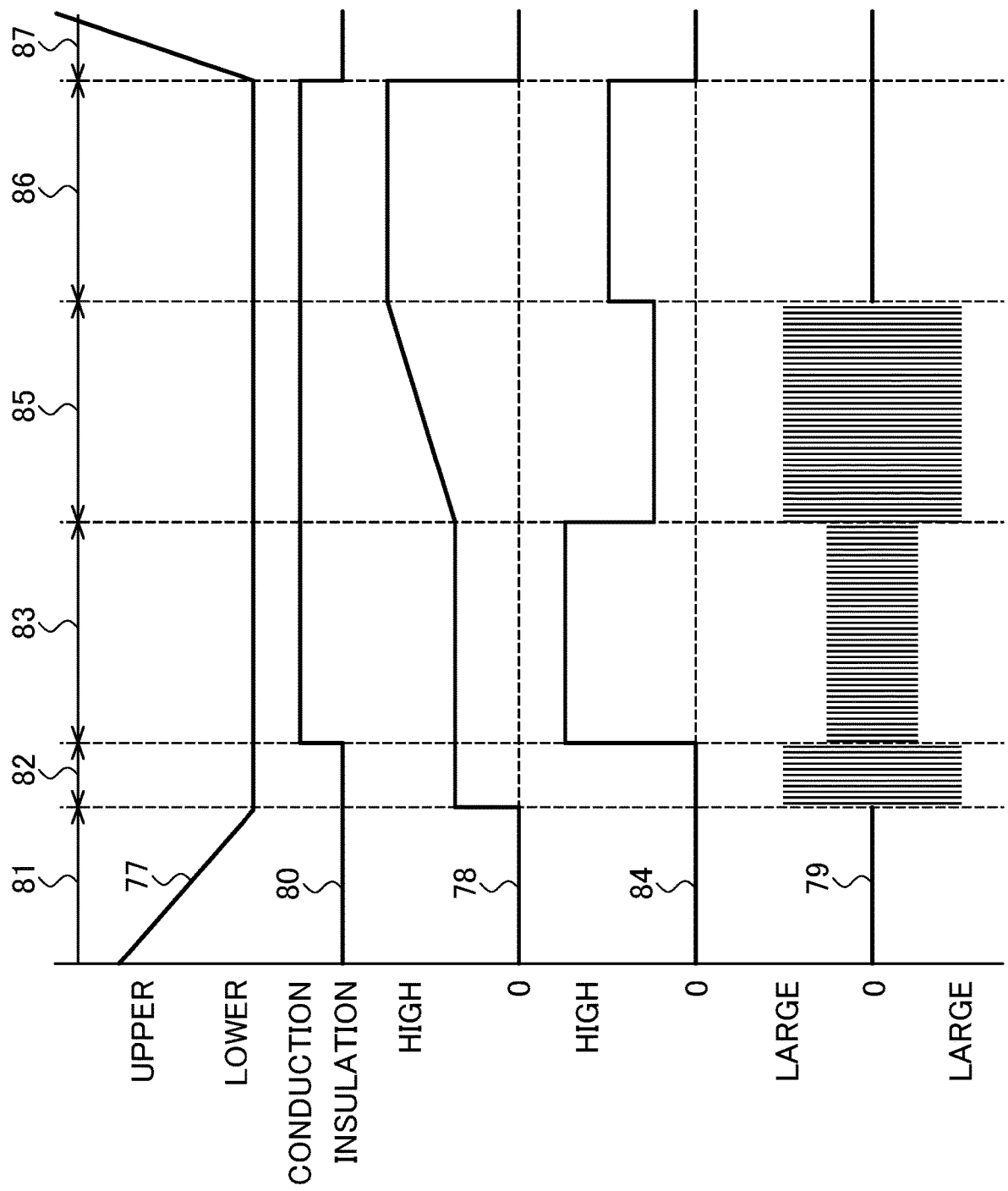
FIG. 15 is a timing chart for describing the operation illustrated in FIGS. 14(A)-14(K).

FIG. 14 are schematic views for describing the operations of the wire bonding apparatus illustrated in FIG. 13 in detail, and are views for describing a method for bonding an insulated coating wire according to one aspect of the present invention. FIG. 15 is a timing chart for describing the operations illustrated in FIG. 14.

In an initial tool lowering stage 81 illustrated in FIG. 15, the capillary (tool) 61 through which the insulated coating wire 11 is inserted is lowered toward a bonding point of the first electrode 12 as indicated by a bonding tool locus 77. Specifically, the tool 61 from which the insulated coating wire 11 protrudes from the tool distal end in an obliquely opposite side of the wire ring is lowered in an oblique direction of the wire ring toward the first electrode 12 as indicated by an arrow 88 (see FIG. 14(A)). In order to reduce and stabilize impact at the landing of the capillary 61, the lowering speed of the capillary 61 is set to a constant low speed.

Next, when the landing of the capillary 61 is detected, the flow proceeds to a dielectric breakdown step 82. A relatively weak pressurizing force 78 and strong ultrasonic power (ultrasonic vibration amplitude 79) are used to apply ultrasonic vibration with large amplitude. The insulated coating is damaged while suppressing the deformation of the core (metal wire) in the insulated coating wire 11 before bonding, leading to swift dielectric breakdown. Specifically, the insulated coating wire 11 is pushed against the first electrode 12 by the tool 61, and ultrasonic vibration of the tool 61 is caused by the ultrasonic horn to break an insulated coating (see FIG. 14(B)). By using the resistance detector 73 to detect the insulated state 80 by the resistance value change caused by small current, unintended heating before bonding and occurrence of electrolytic corrosion on the surface of the capillary 61 during dielectric breakdown are suppressed.

Next, when a conductive state 80 between the capillary 61 and the first electrode 12 through the insulated coating wire 11 in which the insulated coating has been partially broken is detected by the resistance detector 73, the flow proceeds to a bonding surface purification and activation step 83. A low pressurizing force 78 is continued, and a high energization current 84 is caused to flow while suppressing the ultrasonic vibration amplitude 79, so that a part of the insulated coating wire 11 that contacts with the bonding surface of the distal end of the capillary 61 and the first electrode 12 is swiftly heated. In other words, a current is caused to flow from the first electrode 12 to the tool 61, and Joule heat is generated at a metal wire (core) portion of the insulated coating wire 11 pushed against the first electrode 12 by the tool 61 (see FIG. 14(C)). In this manner, the insulated coating is caused to flow due to the heat and the ultrasonic vibration, and is pushed to the outside of the bonding surface. Other organic substances and moisture are simultaneously removed from the bonding surface to form a clean bonding surface for the next bonding operation. The Young's modulus of the bonding portion is decreased by heating, and molecular motion in the bonding surface is activated to activate the surface of the first electrode 12. The energization current value and the energization time are set such that the temperature becomes a temperature (several hundreds of degrees) to cause thermoplastic organic substances constituting the insulated coating at the heated portion, thereby avoiding the remaining of the coating due to insufficient heating, the removal of coating more than necessary due to overheating, and the occurrence of impurities that hinder bonding due to carbonization of the coating. By suppressing the pressurizing force 78 and the ultrasonic vibration amplitude 79, the deformation of the metal core in the insulated coating wire before bonding so as to secure a processing margin. Thus, larger pressurizing force and ultrasonic vibration amplitude can be used during bonding to perform rigid bonding.

After the purification of the bonding surface is completed, the flow proceeds to a bonding step 85. At the bonding step 85, the ultrasonic vibration amplitude 79 is increased and the energization current 84 is decreased to form conditions of ultrasonic thermocompression bonding. In other words, the metal wire (core) in the insulated coating wire 11 and the first electrode 12 are bonded by ultrasonic thermocompression bonding (see FIG. 14(C)). By gradually increasing the pressurizing force 78 as well, the loss of pressure due to a lowering tracking delay of the capillary 11 during the deformation of the core in the insulated coating wire 11 is suppressed to stabilize the bonding.

After the ultrasonic bonding is completed, the flow proceeds to a diffusional growth step 86. The ultrasonic vibration is interrupted while the pressurizing force 78 is maintained to keep the temperature by the energization current 84. Thus, an alloy layer between the core and the first electrode 12 at the bonding portion undergoes diffusional growth to achieve a more rigid bonding state. In this case, the energization current value and the energization time are set to the optimum values in order to avoid damage on the insulated coating wire 11 due to overheating, control the sizes of crystal grains in a recrystallization process of the alloy layer and peripheral metal in the bonding surface, and further improve the bonding strength. In other words, after the bonding surface is formed and the sufficient deformation of the metal wire (core) in the insulated coating wire 11 is obtained, the ultrasonic vibration is stopped, and the alloy layer in the bonding surface is grown with optimized crystal grain sizes by pressurization and energization heating (see FIG. 14(d)).

As illustrated in FIG. 5, when all bonding processes are completed after the diffusional growth step 86, the flow proceeds to a tool raising stage 87. The capillary 11 is raised as indicated by the bonding tool locus 77. Specifically, the energization is stopped and the tool 61 is raised and moved in a wire ring direction indicated by an arrow 89 to form a loop of the insulated coating wire 11 (see FIG. 14(E)).

While feeding the insulated coating wire 11 from the distal end, the tool 61 is lowered in an oblique direction of the wire ring toward the second electrode 90 as indicated by an arrow 92 (see FIG. 14(F)).

The insulated coating wire 11 is pushed against the second electrode 90 by the tool 61, and ultrasonic vibration of the tool 61 is caused by the ultrasonic horn to break the insulated coating (see FIG. 14(G)).

When dielectric breakdown between the tool 61 and the second electrode 90 is detected by the resistance detector, a current is caused to flow from the second electrode 90 to the tool 61 as indicated by an arrow, and Joule heat is generated at a metal wire (core) portion of the insulated coating wire 11 pushed against the second electrode 90 by the tool 61. The insulated coating is caused to flow by the heat and the ultrasonic vibration, and is pushed to the outer side of the bonding surface. Furthermore, the metal wire (core) in the insulated coating wire 11 and the second electrode 90 are bonded by ultrasonic thermocompression bonding (see FIG. 14(H)).

After a bonding surface is formed and sufficient deformation of the metal wire (core) in the insulated coating wire 11 is obtained, the ultrasonic vibration is stopped, and the alloy layer in the bonding surface is grown with optimized crystal grain sizes by pressurization and energization heating (see FIG. 14(i)).

The energization is stopped, and the tool 61 is raised slightly obliquely in the wire ring direction as indicated by an arrow 93, so that the insulated coating wire 11 is clamped by a cut clamp 94 integrated with the tool 61 (see FIG. 14(J)).

While the insulated coating wire 11 is clamped, the tool is raised and moved in the wire ring direction as indicated by an arrow 95 to tear the insulated coating wire 11 at a boundary of the bonding surface (see FIG. 14(K)).

The above-mentioned operations of the wire bonding apparatus are controlled by the controller 75.

According to the present embodiment, when the insulated coating wire 11 is bonded to the electrode 12, the insulated coating at the bonding surface that hinders the bonding can be effectively removed, and a bonding method with high quality and high productivity can be implemented. Many of the existing bonding processes can be used without changing the configuration of the wire bonding apparatus, and hence there is another advantage in that the method is low in cost and high in versatility.

The present embodiment further has the following effects.

(1) It is not necessary to add a heat source around a bonding tool or a workpiece, and hence a conventional wire bonding apparatus can be used as it is. The work area is not narrowed.

(2) By adjusting parameters of pressurization, ultrasonic vibration, and power and time of energization current, processes of dielectric breakdown, bonding surface purification and activation, bonding, and diffusional growth in the bonding process can be separated and individually optimized.

(3) A bonding point with a high relative resistance value generates heat by itself by Joule heat caused by constant current energization, and hence the temperature is swiftly increased and cooled with low thermal capacity. As a result, the heating of the minimum heating region for a short period of time can be performed, and the damage on the insulated coating can be minimized.

(4) By controlling the power supply of energization heating by constant current, the temperature of the heat generating portion can be stabilized to avoid the remaining of coating due to insufficient heating and damage to the coating due to overheating. The functions for setting accurate energization time and varying the energization current value can further optimize the bonding of coated wires.

(5) For local heating by energization heating in which the region and time are limited, ultrasonic thermocompression bonding can be performed without heating a device by a heater plate. As compared with heating by only ultrasonic waves, the ultrasonic thermocompression bonding has an effect to decrease the Young's modulus in the bonding surface and remove moisture that hinders bonding, and hence the diffusional growth in the alloy layer caused by the bonding can be promoted to achieve rigid bonding. By suppressing ultrasonic amplitude, the damage on the tool can be reduced to increase the lifetime of the tool, and hence the reduction in productivity and the increase in running cost due to replacement of the tool can be suppressed. Comprehensively, ultrasonic thermocompression bonding can reduce the damages on wires and devices as compared with thermocompression bonding and ultrasonic bonding.

(6) In the present embodiment in which the coated wire removal process is incorporated in the bonding process, a complicated mechanism unit is not required unlike a method for removing coating at a bonding location of a coated wire in advance, and hence the steps are simple and the productivity is significantly high.

(7) By minimizing the region and time in energization heating, only a portion necessary for coating removal and bonding can be locally heated. This effect provides the suppression of damage on coated wires, and also provides the following effects on bonding targets.

(a) Heat-sensitive materials, such as a resin-based film, a flexible substrate, and a fragile ceramic substrate can be used. The reason is that the entire region is not heated but only a bonding portion can be sufficiently heated.

(b) Materials with low heat conductivity, such as a resin substrate, can be used. The reason is that a bonding portion is not heated through a base material but is directly heated, and hence the temperature can increase swiftly and the peripheral portion has heat insulating properties, with the result that heating efficiency is more improved.

(c) A substrate having a large heat capacity can be used, and can be applied to a power device mounted to a heat sink. The reason is that insufficient total heating is not performed but ultrasonic thermocompression bonding with local heating is performed. As a result, bonding with higher quality can be performed.

The following effects over the conventional bonding methods are obtained.

(1) Solid-phase bonding by ultrasonic waves does not melt materials unlike spot welding and resistance welding, and hence the setting range of parameters of the pressurizing force and current values is wide. Because metal is not melted, the occurrence of fume due to metallic vapor can be prevented. High current is not necessary because of ultrasonic bonding assist heating.

(2) As compared with bonding with only ultrasonic vibration, the mutual agitation by the surface activation by heat and the reduction in Young's modulus at the bonding portion and the growth of the alloy layer enables the bonding strength to be more improved. Due to heat assist, the occurrence of dust due to friction can be prevented by the softening of materials and the suppression of the ultrasonic vibration amplitude.

(3) Almost all parts of the existing facility can be used as it is, and hence the cost can be reduced.

Seventh Embodiment

Figure 16:
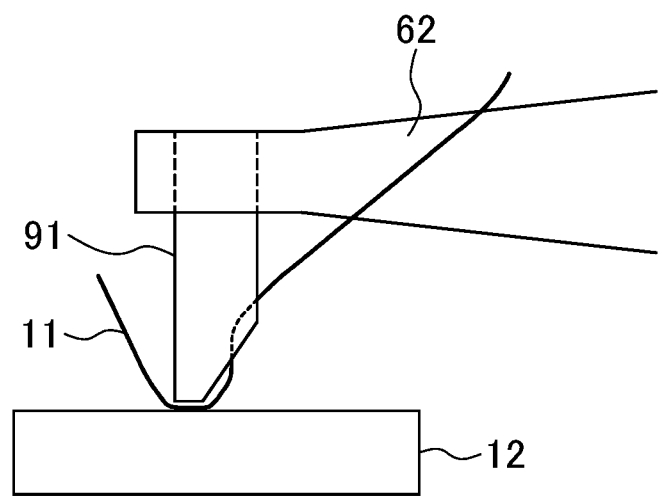
FIG. 16 is a configuration diagram schematically illustrating a part of a wedge bonding apparatus.
Figure 17:
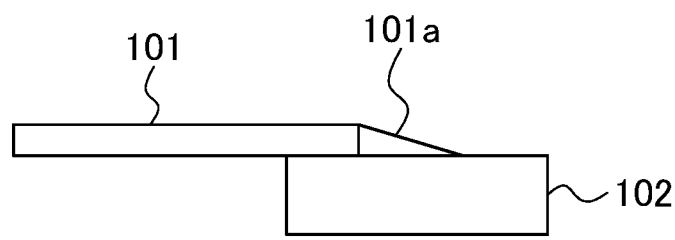
FIG. 17 is a cross-sectional view for describing a conventional method for bonding a distal end of an insulated coating wire to an electrode in a product in semiconductor fields.

FIG. 16 is a configuration diagram schematically illustrating a part of a wedge bonding apparatus. The same parts as in FIG. 13 are denoted by the same reference symbols, and only different parts are described.

In wedge bonding, a wedge bonding tool 91 is used. The other configurations are the same as in the wire bonding apparatus illustrated in FIG. 13, and a bonding process is also the same.

Also in the present embodiment, the same effects as in the sixth embodiment can be obtained.

Note that the first to seventh embodiments can be carried out in combination.

EXPLANATION OF SYMBOLS 10, 10a, 10b distal end of dedicated tool
11 insulated coating wire
11a one end of insulated coating wire
12 first electrode
13, 13a, 13b dedicated tool
14 metal wire (core)
15 bump (first bump)
16, 36 first substrate
21 capillary
22, 42 first electrode
25 first bump
26, 46 second substrate
32,52 second electrode
35, 55 second bump
61 capillary
62 ultrasonic horn
63 motor
64, 65 arrow
66 ultrasonic transducer
67 transducer positive electrode
68 transducer negative electrodes
69 ultrasonic generator
70 constant current source
71 energization positive electrode
72 energization negative electrode
73 resistance detector
74 arrow
75 controller
77 bonding tool locus
78 pressurizing force
79 ultrasonic vibration amplitude
80 conductive state or insulated state
81 tool lowering stage
82 dielectric breakdown step
83 bonding surface purification and activation step
84 energization current
85 bonding step
86 diffusional growth step
87 tool raising stage
88, 89, 92, 93, 95 arrow
90 second electrode
91 wedge bonding tool
94 cut clamp
101 insulated coating wire
101a core (metal wire)
102 electrode

The invention claimed is:

1. A method for bonding an insulated coating wire for electrically connecting a first electrode and a second electrode to each other by an insulated coating wire in which a metal wire is coated with an organic substance, the method comprising:
a step (a) for placing the insulated coating wire onto the first electrode;
a step (b) for exposing a metal wire from the insulated coating wire; and
a step (c) for forming a first bump over the exposed metal wire and the first electrode to electrically connect the metal wire to the first electrode.

2. The method for bonding an insulated coating wire according to claim 1, wherein the step (b) includes pushing the insulated coating wire against the first electrode by a distal end of a tool to expose the metal wire from the insulated coating wire.

3. The method for bonding an insulated coating wire according to claim 2, wherein
the step (b) includes using a bonding apparatus including an ultrasonic horn and an ultrasonic transducer for supplying ultrasonic waves to the ultrasonic horn, holding the tool by the ultrasonic horn, and applying ultrasonic vibration to the tool to expose the metal wire from the insulated coating wire, and
the step (c) includes using the bonding apparatus, holding a capillary through which a wire is inserted by the ultrasonic horn, applying a high voltage between a distal end of the wire protruding from a distal end of the capillary and a discharge electrode to cause discharge, and melting a distal end portion of the wire by discharge energy thereof to form the first bump.

4. The method for bonding an insulated coating wire according to claim 1, wherein the step (a) includes placing an insulated coating wire fed from a distal end of a capillary in a bonding apparatus onto a first position, and moving the capillary to a second position while feeding the insulated coating wire from the distal end of the capillary to place the insulated coating wire onto the first electrode.

5. The method for bonding an insulated coating wire according to claim 1, comprising, before the step (a):
a step for placing an insulated coating wire fed from a distal end of a capillary in a bonding apparatus onto a second electrode, and pushing the insulated coating wire against the second electrode by a distal end of a tool to expose the metal wire from the insulated coating wire; and
a step for forming a second bump over the exposed metal wire and the second electrode to electrically connect the metal wire to the second electrode,
wherein the step (a) includes moving the capillary while feeding the insulated coating wire from the distal end of the capillary to place the insulated coating wire onto the first electrode.

6. The method for bonding an insulated coating wire according to claim 1, wherein the step (a) includes pushing the insulated coating wire fed from a distal end of a capillary in a bonding apparatus against the first electrode with a pressurizing force, and the step (b) includes detecting that the capillary and the first electrode become a conductive state through a metal wire in the insulated coating wire at an adhesion portion between the insulated coating wire and the first electrode due to ultrasonic vibration of an ultrasonic horn in the bonding apparatus, and thereafter causing a current to flow between the capillary and the first electrode to heat the metal wire at the adhesion portion, thereby moving the insulated coating to outside of the adhesion portion and stripping the insulated coating from the insulated coating wire.

7. A method for striping an insulated coating wire, comprising:

a step (a) for pushing an insulated coating wire fed from a distal end of a capillary in a bonding apparatus against a first electrode by pressurization;

a step (b) for detecting that the capillary and the first electrode become a conductive state through a metal wire in the insulated coating wire at an adhesion portion between the insulated coating wire and the first electrode due to ultrasonic vibration of an ultrasonic horn in the bonding apparatus; and a step (c) for causing a current to flow between the capillary and the first electrode to heat the metal wire at the adhesion portion, thereby moving the insulated coating to outside of the adhesion portion and stripping the insulated coating from the insulated coating wire.

8. A method for bonding an insulated coating wire, comprising, after the insulated coating in the insulated coating wire is stripped by using the method for stripping an insulated coating wire according to claim 7, a step (d) for causing a current to flow between the metal wire and the first electrode at the adhesion portion, and controlling the ultrasonic horn to perform ultrasonic vibration to apply ultrasonic vibration to the metal wire and the first electrode through the capillary, thereby electrically connecting the metal wire to the first electrode.

9. The method for bonding an insulated coating wire according to claim 8, comprising, after the step (d), a step (e) for stopping the ultrasonic vibration, and causing a current between the metal wire and the first electrode while pressurizing the metal wire at the adhesion portion against the first electrode by the capillary, thereby growing an alloy layer of the metal wire and the first electrode to enhance bonding strength.

10. The method for bonding an insulated coating wire according to claim 8, comprising, after the step (d) or the step (e), a step (f) for forming a bump over the metal wire and the first electrode to electrically connect the metal wire to the first electrode by the bump.

11. A method for bonding an insulated coating wire, comprising:

a step (c) for pushing, at an adhesion portion between an insulated coating wire fed from a distal end of a capillary in a bonding apparatus and a first electrode, a metal wire exposed while an insulated coating of the insulated coating wire is stripped against the first electrode by the capillary; and a step (d) for causing a current to flow between the capillary and the first electrode and causing a current to flow between the metal wire and the first electrode at the adhesion portion, and controlling an ultrasonic horn in the bonding apparatus to perform ultrasonic vibration to apply ultrasonic vibration to the metal wire and the first electrode through the capillary, thereby electrically connecting the metal wire to the first electrode.

\* \* \* \* \*